United States Patent [19]

Solomon et al.

[11] Patent Number: 5,061,738

[45] Date of Patent: Oct. 29, 1991

[54] BLOOD COMPATIBLE, LUBRICIOUS ARTICLE AND COMPOSITION AND METHOD THEREFOR

[75] Inventors: Donald D. Solomon, Spring Valley; Robert A. Taller, Centerville; Victor A. Williamitis, Dayton, all of Ohio

[73] Assignee: Becton, Dickinson and Company, Franklin Lakes, N.J.

[21] Appl. No.: 639,848

[22] Filed: Jan. 11, 1991

Related U.S. Application Data

[62] Division of Ser. No. 182,694, Apr. 18, 1988, Pat. No. 5,013,717.

[51] Int. Cl.$^5$ ............ A61M 5/32; A61M 25/00; A61M 25/10
[52] U.S. Cl. ............ 523/100; 427/2; 604/265; 514/56; 514/822; 514/953; 424/422; 424/430
[58] Field of Search ............ 514/56, 953, 822; 523/100; 424/422, 430; 427/2; 604/265

[56] References Cited

U.S. PATENT DOCUMENTS

| | | | |
|---|---|---|---|
| 4,326,532 | 4/1982 | Hammar | 514/56 |
| 4,529,614 | 7/1985 | Burns | 514/63 |
| 4,676,975 | 6/1987 | McGary et al. | 514/822 |
| 4,678,468 | 7/1987 | Hiroyoshi | 623/1 |
| 4,720,521 | 1/1988 | Spielvogel et al. | 524/862 |
| 4,925,668 | 5/1990 | Khan et al. | 424/422 |

OTHER PUBLICATIONS

Dow Corning 360 Medical Fluid, Product Bulletin: 51-374 B May 1982, Dow Corning Corporation, Midland, Mich.

Petrach Systems, Bristol, Pennsylvania, Conventional Silicone Fluids.

*Primary Examiner*—Ronald W. Griffin
*Attorney, Agent, or Firm*—Richard E. Brown

[57] ABSTRACT

A leach resistant composition includes a quaternary ammonium complex of heparin and a silicone. A method for applying a coating of the composition to a surface of a medical article is within the purview of the present invention. Medical articles having surfaces which are both lubricious and antithrombogenic, are produced in accordance with the method hereof.

6 Claims, No Drawings

BLOOD COMPATIBLE, LUBRICIOUS ARTICLE AND COMPOSITION AND METHOD THEREFOR

This is a division, of application Ser. No. 07/182,694, filed 4-88, now U.S. Pat. No. 5,013,717.

BACKGROUND OF THE INVENTION

1. Field of the Invention

This invention relates to medical articles, and more particularly relates to a lubricious and antithrombogenic composition and method for its application to a medical article.

2. Background of the Invention

Extensive investigations have been undertaken over many years to find material that will be biologically and chemically stable toward body fluids. This area of research has become increasingly important with the development of various objects and articles which may come into contact with blood, such as artificial organs, vascular grafts, probes, cannulas, catheters and the like.

Synthetic plastics have come to the fore as preferred materials for such articles. However, such materials have the major drawback of being thrombogenic. Even such plastics as polytetrafluoroetheylene and the silicone rubbers, which are more compatible with blood than most plastics, still show thrombogenic characteristics.

Often, use of such articles, as for example, probes, cannulas, catheters and the like, include puncture and passage of the article through the skin. Friction between the patient's skin and the plastic surface of the article may cause substantial discomfort to the patient. Further, catheters are often used in conjunction with an introducer device which typically contains a fost rubber one-way check valve through which the catheter must be threaded. When one surface of an article must slide across another surface, friction may develop which can cause damage to the article. In particular, fragile catheter balloons may be damaged by friction during passage through the valve of the introducer. Thus, both antithrombogenicity and lubricity are highly desirable properties for article surfaces to come into contact with blood.

Surfaces may be rendered lubricious by simple application of any common lubricant. Silicone oils are generally recognized to be among the best lubricants available. Application of a silicone lubricant to a surface is known to result in significant reduction in the surface drag upon catheter insertion, facilitate catheter placement, and reduce the force required for catheter retraction. However, a silicone lubricant coated over a heparinized surface in accordance with the prior art masks the heparin and severely compromises its antithrombogenic activity.

Thrombogenicity has conventionally been counteracted by the use of anticoagulants such as heparin. A variety of heparinization procedures have been reported. For example, Solomon et al., in U.S. Pat. No. 4,521,564, discloses a method to convalently bond heparin to a polyurethane substrate. Eriksson et al., in U.S. Pat. No. 4,118,485, coats a plastic surface with a complex of heparin and either an alkylamine salt or a quaternary amine salt and subsequently stabilizes the heparin by crosslinking with a dialdehyde.

Williams et al., in U.S. Pat. No. 4,613,517, reveals a process for ionically bonding heparin to a polymeric surface including the steps of plasma-treating the surface, absorbing a surface active agent onto the plasma-treated surface, reacting the surface active agent with heparin, and crosslinking the heparin with glutaraldehyde.

Substrates rendered blood compatible by coating with a layer of silicone have been disclosed. Durst et al. in *Am. J. of Roent., Radium Ther. and Nuclear Med.*, 120, 904 (1974) reported that, *in vitro*, siliconized stainless steel guidewires, polytetrafluoroethylene coated guidewires and polyethylene catheters were hypothrombogenic compared to untreated substrates, but, in vivo in dogs, no antithrombogenic effect was observed except with heparin coated substrates.

McGary et al., in U.S. Pat. No. 4,678,660, discloses dipping a polyurethane substrate into a solution of a complex of heparin and tridodecylmethyl ammonium chloride (TDMAC) in polyurethane to form a layer of the complex in polyurethane on the substrate. A lower leach rate of heparin is claimed for the patented product having heparin distributed throughout the polyurethane layer as compared to heparin ionically bonded to TDMAC on the surface of the polyurethane substrate.

U.S. Pat. No. 4,529,614 to Burns discloses coatings of an anticoagulant and a water soluble copolymeric silicone applied to plastic surfaces. The coatings render the surfaces hydrophobic and dissolve in the blood to impart anticoagulant properties to a sample to be analyzed.

Thus, while the prior art has recognized for many years the desirability of rendering substrate surfaces antithrombogenic or lubricious, there are no reports known to the authors of the simultaneous achievement of both effects. The present invention addresses this need.

SUMMARY OF THE INVENTION

One aspect of the invention is a leach resistant composition including an anticoagulant and a lubricant. The preferred anticoagulant is an ammonium complex of heparin. Preferred complexes are quaternary ammonium complexes having at least one long chain alkyl group on the nitrogen, and preferred lubricants are water insoluble silicones having a viscosity range of about 20 to 1,000,000 centistokes. In particularly preferred compositions, the complex has three long chain alkyl groups on the nitrogen and the lubricant is a polydimethylsiloxane of viscosity about 1,000 to 60,000 centistokes.

Another aspect of the invention is a medical device adapted for contact with blood. The device includes a medical article, preferably a shaped medical article having a coating of the composition of the invention on its surface. Preferred medical articles are polymeric, most preferably polyolefin or polyurethane. The most preferred article of the invention is a catheter or catheter introducer having a coating of the composition on its surface.

In another aspect of the invention, a method is provided to coat the surface of the article with the composition so that the surface is both antithrombogenic and lubricious. In the preferred method, the article is coated by dipping into a solvent solution of the composition.

Thus, the invention solves two problems simultaneously which the prior art has addressed only individually. For example, general intravascular catheters coated with the composition of the invention may be inserted easily into the body consequent to the lubricating silicone and, once inserted, exhibit enhanced hemocompatibility consequent to the heparin. If used as a coating on balloon intravascular catheters, the composition, in addition to the above advantages, provides easier insertion of the balloon segment of the catheter thereby decreasing the potential for damage to the balloon during insertion. Further, large gauge and/or multilumen catheters coated with the composition of the invention may be inserted through a rubber introducer valve with minimal damage to the balloon and reduced abrasive removal of a heparin coating.

A particular advantage to coating a medical article with the composition of the invention is that the admixture of heparin and silicone provides lubricity due to the silicone with no compromise of the antithrombogenic activity of the heparin. The water insolubility of the silicone renders the composition resistant to leaching by blood so that antithrombogenicity is retained for periods of up to seven days, and even longer, during medical procedures such as long term catheterization.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In one aspect of the present invention, there is provided a medical device having a surface which is both antithrombogenic and lubricious. The device includes a shaped medical article and a leach-resistant composition on the surface thereof, and, in another aspect of the invention, there is provided an antithrombogenic and lubricious composition. In still another aspect of the invention, a method for rendering a substrate surface both antithrombogenic and lubricious is provided.

The invention will be described in terms of a tubing, such as a catheter; however, it will be apparent to one ordinarily skilled in the art that the substrate may equally be any of a variety of other shaped medical articles. Exemplary, but not limitative, of suitable articles are peripheral and central catheters of all types, including large gauge and multilumen types, introducers and check valves therefor, sheaths, guide wires and stylets. The invention also contemplates applying the composition to either or both of an exterior or interior surface of an article.

The lubricated, antithrombogenic tubing of the invention is preferably made of a polymeric material, though it is appreciated by one skilled in the art that other materials, such as glass, metal or ceramic may be used. Suitable polymers are, for example, polyolefins such as polyethylene or polypropylene, polyvinyl resins such as polyvinylchloride, polyvinylacetate, polyvinylidene fluoride and copolymers thereof, fluorinated polymers such as polytetrafluoroethylene (PTFE), fluorinated ethylenepropylene polymer (FEP) and polytrifluorochloroethylene, polyurethanes, polyamides, silicone elastomers, polystyrenes, styrene-butadiene copolymers, polysiloxane modified polystyrenes and polystyrene-polyolefin copolymers, and thermoplastic interpenetrating network polymers. In addition, the tubing may have an additional coating, such as a hydrogel, on its surface, and the composition of the invention may be applied over the hydrogel coating.

The composition of the invention includes an antithrombogenic agent and a lubricant. Exemplary of suitable antithrombogenic agents are prostaglandins, urokinase, streptokinase, tissue plasminogen activator and heparinoids such as heparin sulfate, dextran sulfate and other sulfonated polysaccharides. The preferred antithrombogenic agent is heparin. Although heparin in any form may be admixed with the lubricant, it is preferred to form the composition of the invention from a complex of heparin with an alkylammonium salt of general structure I:

wherein $R_1$ may be selected from the group consisting of an alkyl group of about 7 to 18 carbon atoms and $R_2$, $R_3$ and $R_4$ may independently be selected from the group consisting of hydrogen, an alkyl group of 1 to 18 carbon atoms and an aralkyl group of 7 to 18 carbon atoms and $X^-$ may be a halide ion, such as chloride or bromide.

The preferred salt to be complexed with heparin is a quaternary ammonium salt of formula I in which $R_1$, $R_2$, $R_3$ and $R_4$ may independently be an alkyl group, straight chain or branched, of form 1 to 18 carbon atoms, or an aralkyl group of about 7 to 18 carbon atoms and X may be a negative monovalent ion, such as a halide ion. For example, the commercially available quaternary salt benzalkonium chloride wherein $R_1$ is $C_8H_{17}$, $R_2$ is $C_6H_5CH_2$ and $R_3$ and $R_4$ are methyl may be used. In particularly preferred quaternary salts for complexation with heparin, $R_1$, $R_2$ and $R_3$ may independently be straight chain alkyl groups of from 8 to 18 carbon atoms and $R_4$ may be lower alkyl group of from 1–4 carbon atoms. In the most preferred salt, $R_1$, $R_2$ and $R_3$ are dodecyl groups, $R_4$ is methyl and $X^-$ is chloride. This quaternary salt is commonly referred to as TDMAC. Thus, the most preferred complex has the formula I wherein $X^-$ is an anion of heparin. Such complexes of heparin are well-known in the art, and are described in McGary et al. and Eriksson et al., supra.

The complex as previously described and silicone are mixed to form the composition of the invention. If the complex has sufficient solubility in the silicone, the mixing may be done merely by dissolving the complex in the silicone at the desired concentration. Preferably, the complex and silicone may be mixed merely by dissolving in an appropriate solvent or solvent system. Use of a solvent is particularly advantageous when a silicone oil of high viscosity is included in the composition. Exemplary of suitable solvents are toluene, petroleum ether, methylene chloride or any one of the fluorinated hydrocarbons conventionally termed Freon ™. In some cases, it may be desirable to use a more polar solvent such as ethanol or isopropanol in the solvent system to aid in dissolution of the complex. The concentration of the complex in the solvent system is not critical, and may advantageously be from about 0.1 to 5% by weight. Higher concentration may be used but generally do not provide any advantage. The preferred concentration is from about 1-2%. Determination of a suitable solvent and concentration for the complex is well within the purview of one ordinarily skilled in the art.

A lubricating oil is added to the solvent solution of the complex. Any water insoluble lubricating oil may be used, as, for example, refined white oil. Preferred lubricants are stable, noncuring high purity medical grade silicones such as the polydialkylsiloxanes of formula II:

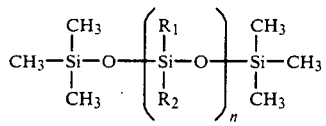

In formula II, $R_1$ and $R_2$ may be independently and alkyl group of from 1 to 20 carbon atoms or taken together may form a ring of from 4 to 8 carbon atoms. The number of repeating units, n, is sufficient to provide a viscosity of from about 20 to 1,000,000 centistokes. In particularly preferred polydialkylsiloxanes of formula II, $R_1$ is methyl and the viscosity is from about 1,000 to 60,000 centistokes. The most preferred silicones are polydimethylsidoxanes having a viscosity of from about 5,000 to 20,000 as exemplified by the commercially available product DC-360 TM available from Dow Corning, Midland, Mich.

The quantity of silicone to be added to the solvent solution of the complex may be varied over a wide range. It has been found that a composition having as little as 2% by weight of the silicone, based on the complex, yields a significant improvement in lubricity when applied to the substrate, as described below. On the other hand, as much as 75% by weight of silicone may be advantageous for certain compositions and substrates. A preferred concentration range of silicone may be from about 20-50% by weight of the complex.

Application of the composition of complex and silicone to the substrate may be carried out by any conventional technique. For example, the composition, preferably in the solvent, may be brushed or sprayed onto the substrate. The preferred method of application is merely to immerse the substrate into the solvent containing the composition. If the substrate is a tubing, such as a catheter, and it is desired to ensure that the composition coats the lumen wall, it may be advantageous to draw the composition into the lumen by the application of reduced pressure.

Immersion of the substrate in the solvent solution of the composition may be carried out at any suitable temperature up to the boiling point of the solvent and may be maintained for any convenient length of time. The time and temperature of contact are not critical, but preferably are about 1 second to 1 hour and ambient temperature.

After withdrawing the substrate from the solution, the solvent may be removed by evaporation. If desired, the rate of evaporation may be accelerated by application of reduced pressure or mild heat. The coating of the composition applied to the substrate may be of any convenient thickness, and in practice, the thickness will be determined by such factors as the viscosity of the silicone, the temperature of the application and the rate of withdrawal. For most substrates, the film preferably is applied as thinly as practical, since no significant advantage is gained by thicker films.

In another embodiment of the invention, the substrate may be treated with a plasma prior to application of the composition. This embodiment of the invention is particularly advantageous for substrates of very low surface energy, such as the fluorinated polymers as exemplified by PTFE and FEP. Suitable conditions for plasma treatment of fluorinated surfaces are described in copending application of common assignee, Ser. No. 081,200, filed Aug. 3, 1987, now abandoned, the disclosure of which is herein incorporated by reference.

When a substrate is coated with the composition of the invention, the surface of the substrate is rendered both antithrombogenic and lubricious, as tested by conventional methods described in the examples. A 1/16 inch (1.6 mm) thick natural rubber membrane may be used as a close approximation of human skin for studies simulating the friction or drag which develops when a catheter, introducer, stylet or guide wire is inserted or withdrawn through the skin of a patient.

Antithrombogenicity for the substrates coated with the composition of the invention may be determined by measuring clotting times by the standard partial (PTT) and activated partial thromboplastin time (APTT) tests (B. A. Brown, *Hematology Principles and Procedures*, Third Edition, Lea and Febiger Co., 1980). These tests are qualitative procedures for determining the efficacy of TDMAC-heparin, as a raw material or as a coating. As a measure of the total anti-clotting activity, the APTT can detect the presence of anticoagulants by giving prolonged clotting times. Non-coated control substrates generally give clotting times of between 25 to 40 seconds. The heparinized tubings of the invention give clotting times greater than 1800 seconds.

The stability of the coatings on the substrates may be determined by performing leach rate studies using normal saline as leachant, as described in Example V.

In vivo thrombus formation on catheters coated with the composition of the invention may be determined by the method of Solomon et al., *J. of Biomedical Materials Research*, 21,43 (1987), as described in Example VI.

This invention will be further described by the following examples, which are illustrative only and not to be considered as limitative. In the examples, the percentages of the complex are given as weight percentages based on the solvent, and the percentages of silicone are weight percentages based on the weight of the complex.

EXAMPLE I

To a 1.25% solution of the heparin-TDMAC complex (McGary et al. supra) in 90:10 Freon TM TF/petroleum ether (v/v), various percentages by weight of 12,500 centistoke silicone oil were added. The solutions were drawn by application of a slight vacuum into the lumens of thermoplastic polyurethane (TPU) catheters of 0.017 and 0.35 in (0.4 and 0.8 mm) inside diameter and 0.92 in (2.3 mm) outside diameter. The solutions were removed and the lumens were dried at 60° C. for 24 hours. Stylet wires were inserted into the lumens of the catheters and then withdrawn at a constant rate of 50 mm/min. The forces required for withdrawal were measured using the Instron Universal Testing Instrument. The results of this experiment are tabulated below in Table I.

TABLE I

| | | | | | | |
|---|---|---|---|---|---|---|
| | | WITHDRAWAL FORCE[a] FOR STYLET WIRE | | | | |
| control | silicone only | silicone only 90 day aging | complex only | complex and 2% silicone | complex and 10% silicone | complex and 30% silicone |
| 4.85 | 0.31 | 0.35 | 5.20 | 11.80 | 0.30 | 0.20 |

TABLE I-continued

WITHDRAWAL FORCE[a] FOR STYLET WIRE

| control | silicone only | silicone only 90 day aging | complex only | complex and 2% silicone | complex and 10% silicone | complex and 30% silicone |
|---|---|---|---|---|---|---|
| 5.25 | 0.34 | 0.31 | 5.30 | 11.50 | 1.50 | 0.12 |
| 6.30 | 0.36 | 0.39 | 7.00 | 11.00 | 0.75 | 0.15 |
| 8.30 | 0.32 | 0.37 | 7.90 | 7.50 | 1.10 | 0.13 |
| 4.90 | 0.39 | | 9.10 | 7.50 | 0.90 | 0.32 |
| 6.70 | 0.35 | | 8.50 | 7.75 | 1.00 | 0.33 |
| | 0.28 | | | | | |
| | 0.36 | | | | | |
| | 0.13 | | | | | |
| | 0.34 | | | | | |
| 6.05[b] | 0.32 | 0.36 | 7.17 | 9.51 | 0.92 | 0.21 |

[a] all values are in newtons (1 newton = 102 g)
[b] mean

It is seen that a coating of silicone only greatly reduces the withdrawal force (column 2) and that this effect remains substantially unchanged after 90 days (column 3). Withdrawal forces are somewhat greater when the catheter is coated with the complex only (column 4), and still greater with 2% silicone (column 5). Columns 6 and 7, however, show that very effective lubrication is achieved when higher concentrations of silicone are used, establishing that the complex does not interfere with lubrication by silicone.

EXAMPLE II

Solutions were prepared containing 12.5 g of the TDMAC-heparin complex and DC 360 ™ silicone oil of 12,500 centistrokes viscosity in 1 liter of 90:10 Freon ™ TF/petroleum ether (v/v). Fifteen cm sections of TPU catheters were coated with the composition of the invention by briefly dipping into the solution, quickly withdrawing in less than one second, and drying at 60° C. for 24 hours. The catheter sections were pulled at a constant speed of 50 mm/min through the rubber check valve of a catheter introducer and the drag forces measured on an Instron Universal Testing Instrument. The results of this experiment are shown in Table II.

TABLE II

CATHETER COATING[a]

| control complex only[b] | control silicone only[c] | complex and 2.98% silicone | complex and 7.50% silicone | complex and 14.88% silicone | complex and 24.76% silicone | complex and 44.64% silicone | complex and 75.0% silicone |
|---|---|---|---|---|---|---|---|
| 561 | 332 | 280 | 277 | 224 | 243 | 127 | 148 |
| 600 | 168 | 316 | 248 | 209 | 189 | 122 | 111 |
| 408 | 154 | 403 | 306 | 311 | 178 | 189 | 142 |
| 484 | 257 | 288 | 301 | 214 | 187 | 114 | 97 |
| — | 158 | 417 | 306 | 286 | — | 112 | 103 |
| 513[d] | 214 | 341 | 288 | 249 | 199 | 133 | 120 |

[a] all drag force values are given in grams
[b] coated from a 1.25% solution of the complex in 1 liter of 90:10 Freon ™ TF-petroleum ether
[c] coated from a 2% solution of silicone in Freon TF
[d] mean It is seen from Table II that as little as 2.98% of silicone oil in the composition reduces the drag force from an average of 513 grams to 341 grams, and that when the silicone percentage is raised to 75% by weight of the complex, the drag force is reduced to 120 grams, or about 20% of the control. As observed in Example I, the presence of the complex does not interfere with the lubricating property of the silicone.

EXAMPLE III

Pieces of TPU catheter tubing 15 cm long were coated with TDMAC-heparin complex and benzalkonium-heparin complex by the procedure of Example II using the solvents and silicones indicated in Table III. The coefficients of friction of these tubings were determined by a Friction Drag Test Accessory to the Instron Universal Testing Instrument. The results of this experiment are tabulated in Table III.

TABLE III

TUBING FRICTION

| Test No. | Control | TDMAC-heparin a | TDMAC-heparin b | Benzalk.-heparin c | TDMAC-heparin; silicone (2%) 1,000[d] | TDMAC-heparin; silicone (2%) 12,500[d] |
|---|---|---|---|---|---|---|
| 1 | | 1.73 | | 2.32 | | |
| 2 | | 1.57 | | 2.42 | | |
| 3 | 1.32 | 1.58 | 1.43 | 2.06 | 0.96 | 0.68 |
| 4 | 1.46 | 1.73 | 1.46 | 1.96 | 0.48 | 0.56 |
| 5 | 1.45 | 1.89 | 1.79 | 1.84 | 0.69 | 0.70 |
| 6 | 1.00 | 1.68 | 1.43 | 1.86 | 0.86 | 0.59 |
| 7 | 1.31 | 1.69 | 1.53 | 2.07 | 0.75 | 0.63 | a toluene-petroleum ether
b Freon ™ TF-petroleum ether
c isopropanol
[d] viscosity in centistokes It is seen from Table III that a coating of heparin complex increases friction over control value, but that a coating of the compositions having the complex admixed with silicone reduces friction.

EXAMPLE IV

Pieces of TPU catheter tubing 15 cm long were coated with the TDMAC-heparin complex (30 ug/cm$^2$) admixed with silicone of 12,500 centistoke viscosity by dipping into Freon ™ TF solutions and drying for 24 hours at 60° C. A 78 gram weight was applied to a natural rubber membrane, and the membrane was dragged across the catheters. Coefficients of friction were determined with the Instron Universal Testing Instrument.

Clotting times for these coated catheter sections were determined by the standard APTT. The results of this experiment are shown in Table IV.

TABLE IV

| % silicone | coefficient of friction | APTT (sec) |
|---|---|---|
| 0 | 1.35 | 1800 |
| 2 | 0.63 | 1800 |
| 5 | 0.25 | 1800 |
| 10 | 0.28 | 1800 |
| 20 | 0.16 | 1800 |
| 30 | 0.19 | 1800 |
| 50 | 0.13 | 1800 |
| 100 | 0.077 | 33 |

Table IV shows that the coefficient of friction decreases with increasing percentage of silicone, but no decrease is seen in clotting time up to 50% silicone percentage, showing that the anticoagulant effect of the heparin is not compromised by the silicone.

EXAMPLE V

Leach Rate Study

Sections of TPU catheters 15 cm long were coated with the TDMAC-heparin complex containing tritiated heparin, with and without admixed silicone oil, by dipping into 2.0 or 1.25 weight percent solutions of the TDMAC complex in the solvents indicated in Tables V and VI. The sections were dried for 24 hours at 60° C., and the quantity of heparin on the catheter surfaces was determined (by liquid scintillation counting and comparison with a standard curve) and expressed as ug heparin/$cm^2$. The coated sections were dynamically leached in 1 l of normal saline using an incubator shaker at 37° C. and 150 rpm for up to seven days. Saline was changed daily, and samples were removed every 24 hours and tested for heparin remaining. PTT and APTT times were also determined.

The results of this experiment are given in Tables V (APTT times) and Table VI (leach rate study). All PTT times for all catheter sections were greater than 1800 sec. APTT times are tabulated in Table V and heparin remaining is shown in Table VI.

TABLE V

APTT TIMES (in seconds)*

| Days | 2% complex$^a$ | 1.25% complex$^a$ | 1.25% complex$^b$ | 1.25% complex$^b$ 2% silicone | 1.25% complex$^b$ 10% silicone | 1.25% complex$^b$ 30% silicone |
|---|---|---|---|---|---|---|
| 0 | 1800 | 1800 | 1800(6) | 1800 | 1800 | 1800 |
| 1 | 1800 | 1800 | 1800(3) | | 1800 | |
| | | | 50.5(3) | 51.1 | | 160.3 |
| 2 | 1800(1) | 1800 | 1800(6) | | 1800 | 1800 |
| | 360(2) | | | 980.0 | | |
| 3 | 1800 | 1800 | 1800 | — | 1800 | — |
| 6 | 1800(1) | 1800(2) | 1800(5) | 1800(2) | — | |
| | 120(2) | 240.(1) | 720.0(1) | 720.0(1) | | 560.0 |
| 7 | | 1800(2) | 1800(1) | | 1800(1) | |
| | 370.0 | 90.0(1) | 75.0(3) | 96.7 | 255.0(2) | 340.3 |

$^a$in toluene - petroleum ether
$^b$in Freon TM - petroleum ether

TABLE VI

LEACH RATE STUDY
Heparin Remaining (ug/$cm^2$)

| Days | 2% complex$^a$ | 1.25% complex$^a$ | 1.25% complex$^b$ | 1.25% complex$^b$ 2% silicone | 1.25% complex$^b$ 10% silicone | 1.25% complex$^b$ 30% silicone |
|---|---|---|---|---|---|---|
| 0 | 33.64 | 14.46 | 16.68 | 13.54 | 17.31 | 11.55 |
| 1 | 16.25 | 5.09 | 8.07 | 3.09 | 6.26 | 8.72 |
| 2 | 12.98 | 7.20 | 6.22 | 5.92 | 7.34 | 7.10 |
| 3 | 5.50 | 8.29 | 5.09 | — | 5.85 | — |
| 6 | 5.63 | 1.77 | 3.77 | 4.58 | 3.72 | 3.52 |
| 7 | 4.45 | 2.85 | 3.05 | 2.67 | 2.69 | 4.33 |

$^a$in toluence - petroleum ether
$^b$in Freon TM - petroleum ether

The results of Example V show that even when the heparin remaining on the catheter sections has been reduced to as low as 2-3 ug/$cm^2$ by a seven day saline leach, the PTT and APTT times are still more than 1800 seconds.

EXAMPLE VI

TPU catheters (16 gauge) were coated with the heparin-silicone composition of the invention and studied by the in vivo method for evaluation of catheter thrombogenicity of Solomon et al. (supra). Uncoated TPU catheters and polyvinyl chloride catheters (PVC, 16 gauge) served as controls in this experiment. Counts were plotted against time and the curve slopes were determined.

TABLE VII

| Catheter Material | Slope |
|---|---|
| PVC | 0.118 ± 0.077 |
| TPU | 0.077 ± 0.042 |
| heparinized TPU | 0.012 ± 0.010 |

The significant decreases in the number of counts (deposited platelets) with time is readily apparent from the lower slope of the curve with the heparinized TPU of the invention.

Thus, in accordance with the invention, the surfaces of medical articles adapted for contact with blood and friction-generating movement across another surface or a patient's skin may be coated with a composition of anticoagulant, preferably heparin, and silicone. The heparin provides blood compatibility and the silicone provides lubricity without in any way compromising the anticoagulant activity of the heparin. Because the silicone is water insoluble, the composition is resistant to leaching by the blood and remains on the surface of the device for prolonged periods. This is a particular advantage for medical procedures, such as long term catheterizations, and provides both safety and comfort to the patient.

What is claimed is:

1. A medical device for contact with a blood stream comprising an article having coated thereon a composition comprising a mixture of a quaternary ammonium complex of heparin and about 2 to 75% by weight of a noncuring lubricating silicone, said complex having the formula

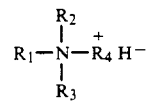

wherein $R_1$, $R_2$, $R_3$ and $R_4$ are independently selected from the group consisting of an alkyl group of 1 to about 18 carbon atoms and an aralkyl group of about 7 to 18 carbon atoms and $H^-$ is a negative ion of heparin, said silicone having a viscosity of about 20 to 1,000,000 centistokes.

2. The device of claim 1 wherein said viscosity is from about 1,000 to 60,000 centistokes.

3. The device of claim 1 wherein $R_1$, $R_2$ and $R_3$ are independently alkyl groups selected from the group having 8 to 18 carbon atoms and $R_4$ is an alkyl group selected from the group having from 1 to 4 carbon atoms.

4. The device of claim 1 wherein said article is a catheter.

5. The device of claim 1 wherein said device is a catheter introducer.

6. A medical device of claim 1 for contact with a blood stream comprising a shaped article having coated thereon a composition comprising a mixture of a quaternary ammonium complex of heparin and about 20 to 50% by weight of a noncuring lubricating polydimethylsiloxane, said complex having the formula

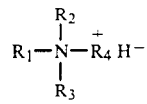

wherein $R_1$, $R_2$ and $R_3$ are independently selected from the group consisting of a straight chain alkyl group of 8 to 18 carbon atoms, $R_4$ is selected from the group consisting of a lower alkyl group of 1 to 4 carbon atoms and $H^-$ is a negative ion of heparin, said polydimethylsiloxane having a viscosity of about 1,000 to 60,000 centistokes.

* * * * *